(12) United States Patent
Dragan et al.

(10) Patent No.: US 7,323,483 B2
(45) Date of Patent: Jan. 29, 2008

(54) PROCESSES AND COMPOUNDS FOR THE PREPARATION OF SUBSTITUTED NAPHTHYLINDOLE DERIVATIVES

(75) Inventors: Vladimir A. Dragan, Chester, NY (US); John Richard Potoski, West Nyack, NY (US); Wayne G. McMahon, Harriman, NY (US); Jean Louise Helom, Hillsdale, NJ (US); Xinxu Shi, Flushing, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/339,802

(22) Filed: Jan. 25, 2006

(65) Prior Publication Data
US 2006/0183917 A1 Aug. 17, 2006

Related U.S. Application Data

(60) Provisional application No. 60/647,618, filed on Jan. 27, 2005.

(51) Int. Cl.
*A61K 31/404* (2006.01)
*C07D 257/04* (2006.01)
(52) U.S. Cl. ...................... 514/381; 548/254
(58) Field of Classification Search ............... 514/381; 548/254
See application file for complete search history.

(56) References Cited

U.S. PATENT DOCUMENTS

| | | | |
|---|---|---|---|
| 5,151,435 A | 9/1992 | Bagley et al. | 514/303 |
| 6,800,654 B2 | 10/2004 | Mayer et al. | 514/381 |
| 6,939,886 B2 * | 9/2005 | Mayer et al. | 514/381 |
| 2002/0198411 A1 | 12/2002 | Tanikawa et al. | 568/391 |

FOREIGN PATENT DOCUMENTS

| | | |
|---|---|---|
| EP | 0 416 609 | 3/1991 |
| EP | 0 508 723 | 10/1992 |
| EP | 0 512 570 | 11/1992 |
| EP | 0 655 439 | 5/1995 |
| WO | WO 94/26738 | 11/1994 |
| WO | WO 95/10513 | 4/1995 |
| WO | WO 96/21656 | 7/1996 |
| WO | WO 97/09308 | 3/1997 |
| WO | WO 98/08818 | 3/1998 |
| WO | 03/000649 A1 | 1/2003 |
| WO | 03/000684 A1 | 1/2003 |

OTHER PUBLICATIONS

Ooi, T., et al., "Practical Oppenauer (OPP) Oxidation of Alcohols with a Modified Aluminum Catalyst," *Organic Letters*, 2002, 4, 2669-2672.
Smith, M.B. and March, J., *Advanced Organic Chemistry*, Wiley 5th ed. 2001, pp. 496, 503, 520, and 528.
Aznar, J. et al., "Role of Plasminogen Activator Inhibitor Type 1 in the Pathogenesis of Coronary Artery Diseases," *Haemostasis* 24: 243-251 (1994).
Biemond, B.J. et al., "Thrombolysis and Reocclusion in Experimental Jugular Vein and Coronary Artery Thrombosis," *Circulation*, 91: 1175-1181 (1995).
Carmeliet, P. et al., "Plasminogen Activator Inhibitor -1 Gene-deficient Mice," *Journal of Clinical Investigation*, 92: 2756-2760 (Dec. 1993).
Daci, E. et al., "Mice Lacking the Plasminogen Activator Inhibitor 1 are Protected from Trabecular Bone Loss Induced by Estrogen Deficiency," *Journal of Bone and Mineral Research*, 15(8):1510-1516 (Nov. 8, 2000).
Krishnamurti, C. et al., "Plasminogen Activator Inhibitor: A Regulator of Ancrod-Induced Fibrin Deposition in Rabbits," *Blood*, 69(3): 798-803 (Mar. 1987).
Levi, M. et al., "Inhibition of Plasminogen Activator Inhibitor-1 Activity Results in Promotion of Endogenous Thrombolysis and Inhibition of Thrombus Experimental Thrombosis," *Circulation* 85, 305-312 (1992).
Nordt, T. K. et al., "Differential Regulation by Troglitazone of Plasminogen Activator Inhibitor Type 1 in Human Hepatic and Vascular Cells," *Journal of Clinical Endocrinology and Metabolism*, 85(4):1563-1568 (2000).
Reilly, C. et al., "Both Circulating and Clot-Bound Plasminogen Activator-1 Inhibit Endogenous Fibrinolysis in the Rat," *Arteriosclerosis and Thrombosis*, 11(5): 1276-1286 (Sep./Oct. 1991).
Rocha, E. et al., "The Relationship Between Impaired Fibrinolysis and Coronary Heart Disease," *Fibrinolysis*, 8: 294-303 (1994).
Aznar et al., "role of Plasminogen Activator Inhibitor Type 1 in the Pathogenesis of Coronary Artery Diseases," *Haemostatis*, 1994, 24, 243-251.
Biemond et al., "Thyrombolysis and Reocclusion in Experimental Jugular Vein and Coronary Artery Thrombosis: Effects of a Plasminogen Activator Inhibitor Type 1-Neutralizing Monoclonal Antibody," *Circulation*, 1995, 91(4), 1175-1181.
Carmeliet et al., "Plasminogen Activator Inhibitor-1 Gene-deficient Mice; II. Effects of hemostasis, Thrombosis, and Thrombolysis," *Journal of Clinical Invest.*, 1993, 92, 2756-2760.
Daci et al., "Mice Lacking the Plasminogen Activator Inhibitor 1 Are Protected from Trabecular Bone Loss Induced by Estrogen Deficiency," *Journal of Bone & Mineral Research*, 2000, 15(8), 1510-1516.

(Continued)

*Primary Examiner*—Rebecca Anderson
*Assistant Examiner*—Shawquia Young
(74) *Attorney, Agent, or Firm*—Mabel Ng

(57) ABSTRACT

The present invention provides processes for the preparation of substituted naphthylindole derivatives that can be used as inhibitors of plasminogen activator inhibitor-1(PAI-1). In certain embodiments of the invention, the processes involve reactions that include one or more of an Oppenauer oxidation, a Fischer indole synthesis, a methyl ether cleavage, or coupling a substituted methyltetrazole with a substituted naphthol.

19 Claims, No Drawings

OTHER PUBLICATIONS

Guzzo, P.R. et al., "Synthesis of a conformationally constrained threonin-valine dipeptide mimetic: design of potential inhibitor of plasminogen activator inhibitor-1," *Tetrahedron Letters*, 2002, 43(1), 41-42.

Krishnamurti et al., "Plasminogen Activator Inhibitor: A Regulator of Ancrod-Induced Fibrin Deposition in Rabbits," *Blood*, 1987, 69(3), 798-803.

Levi et al., "Inhibition of Plasminogen Activator Inhibitor-1 Activity Results in Promotion of Endogenous Thrombolysis and Inhibition of Thrombus Extension in Models of Experimental Thrombosis," *Circulaiton*, 1992, 85(1), 305-312.

Nordt et al., "Differential Regulation by Troglitazone of Plasminogen Activator Inhibitor Type 1 in Human Hepatic and Vascular Cells," *The Journal of Clinical Endocrinology & Metabolism*, 2000, 85(4), 1563-1568.

Reilly et al., "Both Circulating and Clot-Bound Plasminogen Activator Inhibitor-1 Inhibit Endogenous Fibrolysis in the Rat," *Arteriosclerosis & Thrombosis*, 1991, 11, 1276-1286.

Rocha et al., "The Relationship Between Impaired Fribinolysis and Coronary Heart Disease: a Role for PAI-1," *Fibrinolysis*, 1994, 8, 294-303.

\* cited by examiner

PROCESSES AND COMPOUNDS FOR THE PREPARATION OF SUBSTITUTED NAPHTHYLINDOLE DERIVATIVES

CROSS REFERENCE TO RELATED APPLICATIONS

This application claims the benefit of U.S. Application Ser. No. 60/647,618, filed Jan. 27, 2005, which is incorporated herein in its entirety.

FIELD OF THE INVENTION

The present invention relates to processes for the preparation of substituted naphthylindole derivatives that can be used, for example, as inhibitors of plasminogen activator inhibitor-1 (PAI-1) to treat deep vein thrombosis, coronary heart disease, pulmonary fibrosis, and other conditions resulting from fibrinolytic disorders.

BACKGROUND OF THE INVENTION

Plasminogen activator inhibitor-1 (PAI-1) is a major regulatory component of the plasminogen-plasmin system. PAI-1 is the principal physiologic inhibitor of both tissue type plasminogen activator (tPA) and urokinase type plasminogen activator (uPA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigation*, 92, 2756 (1993)) and clinical studies (Rocha, *Fibrinolysis*, 8, 294, 1994; Aznar, *Haemostasis* 24, 243 (1994)). Elevated levels of PAI-1 have also been implicated in diseases such as polycystic ovary syndrome (Nordt, *Journal of clinical Endocrinology and Metabolism*, 85, 4, 1563 (2000)) and bone loss induced by estrogen deficiency (Daci, *Journal of Bone and Mineral Research*, 15, 8, 1510 (2000)). Antibody neutralization of PAI-1 activity has been found to result in promotion of endogenous thrombolysis and reperfusion (Biemond, *Circulation*, 91, 1175 (1995); Levi, Circulation 85, 305, (1992)). Accordingly, agents that inhibit PAI-1 would be of utility in treating, for example, conditions originating from fibrinolytic disorders such as deep vein thrombosis, coronary heart disease, pulmonary embolism, and polycystic ovary syndrome. A need exists in the art for processes for the efficient preparation of PAI-1 inhibitors.

SUMMARY OF THE INVENTION

This invention relates to processes for the preparation of substituted naphthylindole derivatives that can be used as inhibitors of plasminogen activator inhibitor-1 (PAI-1), as well as synthetic intermediates useful in such processes.

In preferred embodiments, the invention is directed to processes that comprise reacting a compound of formula (3):

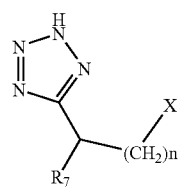

(3)

wherein

X is a leaving group;

$R_7$ is hydrogen, alkyl of 1 to 6 carbon atoms, alkylaryl of 7 to 20 carbon atoms, or aryl of 6 to 14 carbon atoms optionally substituted with 1 to 3 $R_8$ groups;

$R_8$ is hydrogen, alkyl of 1 to 3 carbon atoms, cycloalkyl of 3 to 5 carbon atoms, —$CH_2$cycloalkyl of 4 to 6 carbon atoms, alkanoyl of 2 to 4 carbon atoms, halogen, hydroxy, perfluoroalkyl of 1 to 3 carbon atoms, alkoxy of 1 to 3 carbon atoms, amino, alkylamino of 1 to 3 carbon atoms, dialkylamino of 1 to 3 carbon atoms, or perfluoroalkoxy of 1 to 3 carbon atoms; and n is an integer from 0 to 6;

in the presence of an inorganic or organic base, with a compound of formula (2):

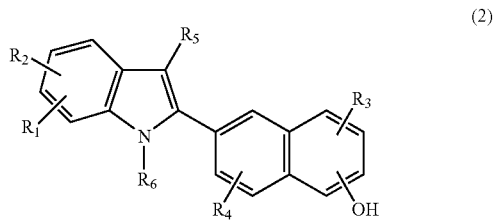

(2)

wherein:

$R_1$, $R_2$, $R_3$, and $R_4$ are each, independently, hydrogen, alkyl of 1 to 3 carbon atoms, cycloalkyl of 3 to 5 carbon atoms, —$CH_2$cycloalkyl of 4 to 6 carbon atoms, alkanoyl of 2 to 4 carbon atoms, halogen, hydroxyl, aryl of 6 to 14 carbon atoms optionally substituted with 1 to 3 $R_8$ groups, perfluoroalkyl of 1 to 3 carbon atoms, alkoxy of 1 to 3 carbon atoms, amino, alkylamino of 1 to 3 carbon atoms, dialkylamino of 1 to 3 carbon atoms, or perfluoroalkoxy of 1 to 3 carbon atoms;

$R_5$ is hydrogen, alkyl of 1 to 6 carbon atoms, perfluoroalkyl of 1 to 6 carbon atoms, aryl of 6 to 14 carbon atoms optionally substituted with 1 to 3 $R_8$ groups, alkanoyl of 2 to 7 carbon atoms, or aroyl of 7 to 15 carbon atoms optionally substituted with 1 to 3 $R_8$ groups; and $R_6$ is hydrogen, alkyl of 1 to 6 carbon atoms, alkylaryl of 8 to 20 carbon atoms, benzyl optionally substituted with 1 to 3 $R_8$ groups, alkanoyl of 2 to 7 carbon atoms, or aroyl of 7 to 15 carbon atoms optionally substituted with 1 to 3 $R_8$ groups; to produce compounds of formula (1):

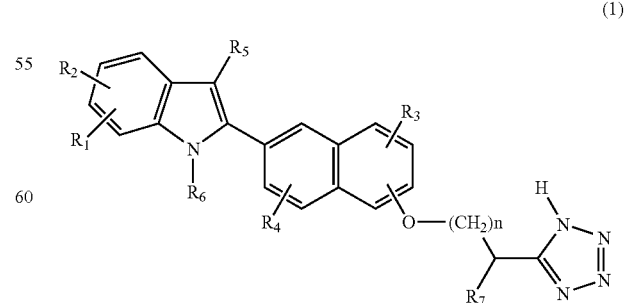

(1)

or pharmaceutically acceptable salts thereof.

Other embodiments of the invention relate to processes that comprise reacting a compound of formula (6):

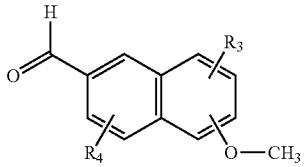

(6)

with an alkylmagnesium halide or an arylmagnesium halide having the formula $R_9MgBr$ and further with a hydride acceptor to produce a compound of formula (5):

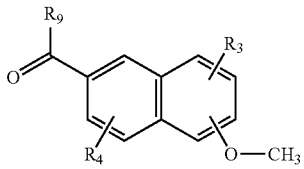

(5)

wherein $R_9$ is —$CH_2$—$R_5$.

In preferred embodiments, a compound of formula (6) is reacted with hexylmagnesium bromide (HxMgBr) and further with 1-methyl-4-piperidone (MPP). Alternatively, compounds of formula (5) can be produced by reacting a compound of formula (6) consecutively with an alkyllithium having the formula $R_9Li$, a magnesium salt, and a hydride acceptor. Preferred embodiments comprise reacting a compound of formula (6) consecutively with hexyllithium, magnesium sulfate, and 1-methyl-4-piperidone (MPP).

Compounds of formula (5), in turn, can be reacted with a substituted hydrazine having the formula

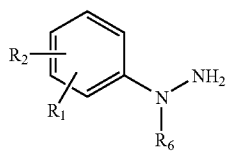

to produce compounds of formula (4):

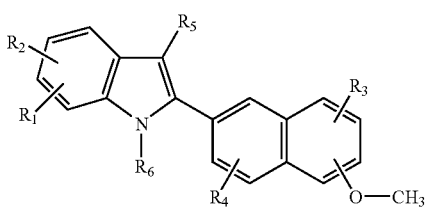

(4)

In certain embodiments of the invention, compounds of formula (4) are reacted with an ether demethylating agent to produce compounds of formula (2) as described above.

The present invention also provides synthetic intermediates and other compounds involved in the foregoing processes, including compounds of formulas (1), (2), (4), (5), and (6).

DETAILED DESCRIPTION OF ILLUSTRATIVE EMBODIMENTS

Certain aspects of the present invention relate to processes for the preparation of substituted naphthylindole derivatives that can be used as inhibitors of plasminogen activator inhibitor-1(PAI-1). Preferred processes of the invention include a direct Oppenauer oxidation on a magnesium alkoxide, allowing a ketone to be directly produced from a starting aldehyde. Further preferred embodiments of the invention relate to processes that include a Fischer indole synthesis in which an N-aryl-N-alkylhydrazine, in which the alkyl substituent is optionally substituted with an aryl group, is reacted with a ketone to directly yield an N-benzylindole. The invention also encompasses processes involving a methyl ether cleavage in which a methoxy group is cleaved with boron tribromide. Other embodiments of the invention relate to processes that involve direct coupling of protected, substituted methyltetrazole with naphthol. In preferred embodiments of the invention, the tetrazole is pyran-protected.

The term "alkyl," as used herein, refers to an aliphatic hydrocarbon chain having up to 12 carbon atoms, preferably 1 to 6 carbon atoms, and more preferably 1 to 3 carbon atoms. The term "alkyl" includes, but is not limited to, straight and branched chains such as methyl, ethyl, n-propyl, isopropyl, n-butyl, isobutyl, sec-butyl, t-butyl, n-pentyl, isopentyl, neo-pentyl, n-hexyl, and isohexyl.

The term "cycloalkyl," as used herein, refers to a saturated carbocyclic group containing 3 to 8 ring carbon atoms, preferably 3 to 5 ring carbon atoms. Cycloalkyl groups may be monocyclic or bicyclic, and are preferably monocyclic.

The term "aryl," as used herein refers to a 6 to 14 membered carbocyclic aromatic ring. Aryl groups may be monocyclic or bicyclic. Monocyclic aryl groups preferably have 6 members and bicyclic aryl groups preferably have 10 members. Exemplary aryl groups include phenyl and naphthyl.

The term "perfluoroalkyl," as used herein, refers to a straight or branched aliphatic hydrocarbon chain of 1 to 6 carbon atoms and preferably 1 to 3 carbon atoms, in which all hydrogens are replaced with fluorine.

The term "alkanoyl," as used herein, refers to the group R—C(=O)— where R is an alkyl group of 1 to 6 carbon atoms, preferably 1 to 3 carbon atoms, as previously defined.

The term "alkoxy," as used herein, refers to the group R—O— where R is an alkyl group of 1 to 6 carbon atoms, preferably 1 to 3 carbon atoms, as previously defined.

The term "perfluoroalkoxy," as used herein, refers to the group R—O— where R is a perfluoroalkyl group of 1 to 6 carbon atoms, preferably 1 to 3 carbon atoms, as previously defined.

The terms "alkylamino" and "dialkylamino," as used herein, respectively refer to —NHR and —$NRR_a$, where R and $R_a$ are independently selected from an alkyl group of 1 to 6 carbon atoms, preferably 1 to 3 carbon atoms, as previously defined.

The term "carboxy," as used herein, refers to the group —COOH.

The terms "halogen" or "halo," as used herein, refer to chlorine, bromine, fluorine or iodine.

The term "alkylaryl," as used herein, refers to the group R-aryl- where R is an alkyl group of 1 to 6 carbon atoms as previously defined, and aryl is an aryl group of 6 to 14 carbon atoms as previously defined.

The term "aroyl," as used herein, refers to the group aryl-C(O)—, where aryl is an aryl group of 6 to 14 carbon atoms as previously defined.

The term "alkaline earth metal," as used herein, refers to beryllium, magnesium, calcium, strontium, barium, or radium.

The terms "inorganic base" and "organic base," as used herein, refer to compounds that react with an acid to form a salt; compounds that produce hydroxide ions in an aqueous solution (Arrhenius bases); molecules or ions that capture hydrogen ions (Bronsted-Lowry bases); and/or molecules or ions that donate an electron pair to form a chemical bond (Lewis bases).

The term "hydride acceptor," as used herein, refers to a chemical entity to which a hydride can be transferred from a hydride donor. The term "hydride donor," as used herein, refers to a chemical entity that can transfer a hydride to a hydride acceptor. Certain hydride acceptors contain a carbonyl group. Hydride acceptors include, for example, cyclohexanone and benzaldehyde. Hydride acceptors are described, for example, in Byrne, B., et al., *Tetrahedron Letters* 28:769-72 (1987); Tanikawa, S., et al., U.S. Pat. Appl. Publ. 2002198411 (2002); and Ooi, T., et al., *Organic Letters* 4:2669-2672 (2002).

The term "ether demethylating agent," as used herein, refers to a chemical entity that is capable of cleaving a methyl ether, as described, for example, in Smith, M. B. and March, J., *Advanced Organic Chemistry*, Wiley 5$^{th}$ ed. 2001, pp. 496, 503, 520, and 528. Ether demethylating agents include, for example, BBr$_3$, Me$_3$SiI, concentrated HBr and HI, sodium N-methylanilide, and thiolate ions.

The term "leaving group," as used herein, refers to a chemical entity that is easily displaced from a methylenetetrazole by a nucleophile. Examples of leaving groups include, but are not limited to, halides, such as, for example, Cl, Br and I; and sulfonates, such as, for example, mesylate, tosylate, and triflate.

Certain embodiments of the invention are directed to processes that involve Oppenauer oxidation. Preferred aspects of the invention relate to Oppenauer oxidation on a magnesium alkoxide, allowing a ketone to be directly produced from an aldehyde. Preferred processes comprise reacting a compound of formula (6):

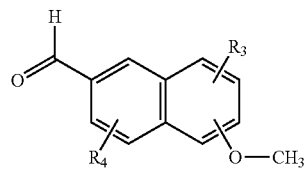

(6)

with an alkylmagnesium halide or an arylmagnesium halide having the formula R$_9$MgBr, and further with a hydride acceptor, to produce a compound of formula (5):

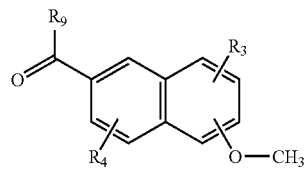

(5)

In preferred embodiments, the alkylmagnesium halide is hexylmagnesium halide, methylmagnesium halide, isobutylmagnesium halide, or benzylmagnesium halide. In particularly preferred embodiments, the alkylmagnesium halide is hexylmagnesium bromide (HxMgBr).

Preferred hydride acceptors include optionally substituted dialkylaminobenzaldehydes and optionally substituted tertiary aminocycloalkanones. Optional substituents for the dialkylaminobenzaldehydes and tertiary aminocycloalkanones include, but are not limited to, electron withdrawing groups such as nitro, cyano, alkoxycarbonyl, and alkylsulfonyl. In particularly preferred embodiments of the invention, the hydride acceptor is 1-methyl-4-piperidone (MPP). Other hydride acceptors useful in the processes of the invention are familiar to those skilled in the art.

Other aspects of the invention relate to processes in which a compound of formula (6) is reacted consecutively with an alkyllithium having the formula R$_9$Li, a magnesium salt, and a hydride acceptor to produce a compound of formula (5). In preferred processes, the alkyllithium is hexyllithium and the magnesium salt is magnesium bromide, magnesium chloride, a magnesium sulfonate, or magnesium sulfate.

Particularly preferred processes involve magnesium alkoxide oxidation, as depicted in Scheme 1, below.

Scheme 1

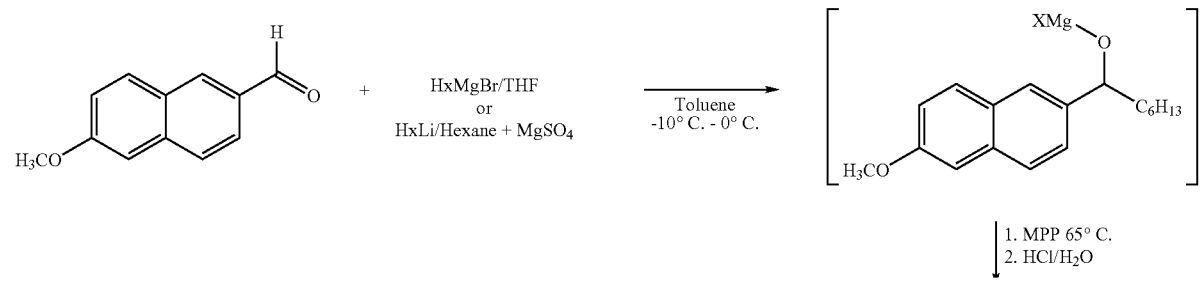

1. MPP 65° C.
2. HCl/H$_2$O

-continued

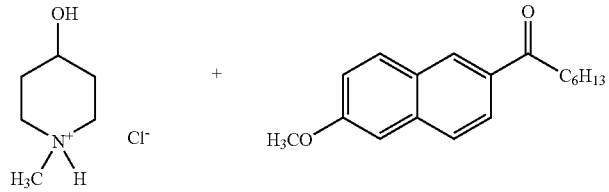

Generally, a solution of 6-methoxy-2-naphthaldehyde in toluene is added to a solution of Grignard regent at 0° C. followed by the immediate addition of 0.3 equivalents of 1-methyl-4-piperidone (MPP). The resulting mixture is heated to 65° C. and treated with 1.8 equivalents of 1-methyl-4-piperidone (MPP) over five hours. The mixture is cooled to ambient temperature and quenched with 10% hydrochloric acid. The aqueous layer is separated and the solvent in the organic layer is exchanged with heptane to yield, upon cooling to −15° C., 80% to 90% of crystalline 1-(6-methoxynaphthalen-2-yl)heptan-1-one.

The reaction depicted in Scheme 1 can be performed using alternative solvents, including hydrocarbons, such as, for example, alkanes and cycloalkanes; aromatic hydrocarbons, such as, for example, xylenes, alkylbenzenes, and alkyltoluenes; ethers, such as, for example, tert-butylmethylether, glymes, substituted furans, and dioxanes; and amides such as, for example, DMF and NMP.

In further aspects of the invention, the reaction temperatures in the process depicted in Scheme 1 are as much as 10° C. higher or lower than that indicated in the description provided above, with the exception of the hexyllithium addition, which typically is not carried out at temperatures higher than −5° C.

The invention also relates to processes that include a Fischer indole synthesis. Preferred processes include a Fischer indole synthesis reaction in which a substituted hydrazine having the formula:

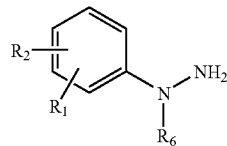

is reacted with a ketone to directly yield an indole. Particularly preferred processes comprise reacting a compound of formula (5):

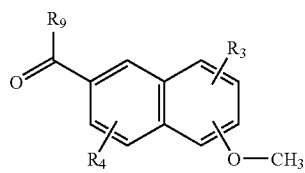

with a hydrazine as described herein to produce a compound of formula (4):

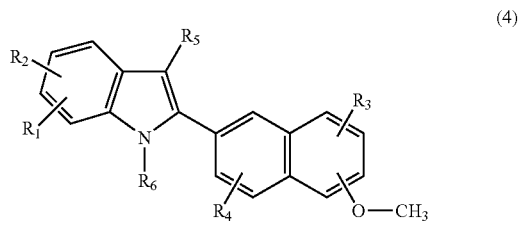

In certain aspects of the invention, the hydrazine is 1-benzyl-1-phenylhydrazine hydrochloride (BPH), 1-methyl-1-phenylhydrazine, or 1-diphenylmethyl-1-(4-methoxyphenyl)hydrazine. In particularly preferred embodiments, the hydrazine is 1-benzyl-1-phenylhydrazine hydrochloride (BPH). Particularly preferred processes are those that involve the reaction depicted in Scheme 2, below.

Scheme 2

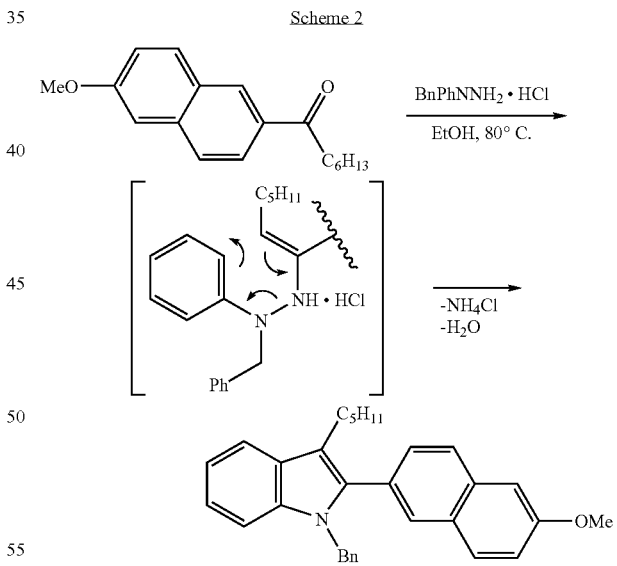

Generally, a suspension of equimolar amounts of 1-(6-methoxynaphthalen-2-yl)heptan-1-one and N-benzyl-N-phenylhydrazine hydrochloride (BPH) in ethanol is heated under reflux for five hours. Two portions of 0.1 equivalent of BPH in ethanol are added to the suspension at one hour intervals. Alternatively, the solution of BPH in ethanol is added to reaction mixture continuously. The resulting mixture is refluxed for an hour, diluted with heptane, and treated with water at 45° C. The organic and aqueous phases are separated, and the organic phase is washed with water and cooled to 10° C. to initiate crystallization. Upon cooling to −15° C., 80%-85% of crystalline 1-benzyl-2-(6-methoxy-naphthalen-2-yl)-3-pentyl-1H-indole is obtained.

The reaction depicted in Scheme 2 can be performed using alternative solvents, including alcohols such as, for example, propanol-1 and propanol-2; nitriles, such as, for example, acetonitrile and propionitrile; and aromatic hydrocarbons, such as, for example, xylenes, alkylbenzenes, and alkyltoluenes.

In further embodiments of the invention, the reaction temperature in the process depicted in Scheme 2 is as much as 30° C. higher than that indicated in the description provided above.

The invention further includes processes that involve methyl ether cleavage. Preferred processes are those in which a methoxy group is cleaved with boron tribromide. Preferred processes comprise reacting a compound of formula (4):

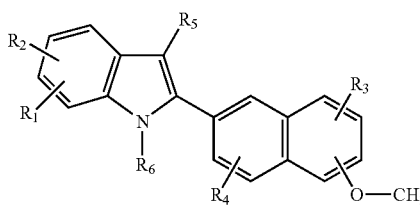

(4)

with an ether demethylating agent to produce a compound of formula (2):

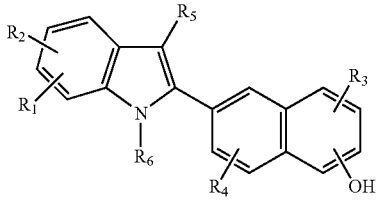

(2)

In preferred processes, the ether demethylating agent is boron tribromide ($BBr_3$). Those skilled in the art are familiar with additional agents suitable for demethylating methyl ethers.

Particularly preferred processes involve methyl ether cleavage, as depicted in Scheme 3, below.

Scheme 3

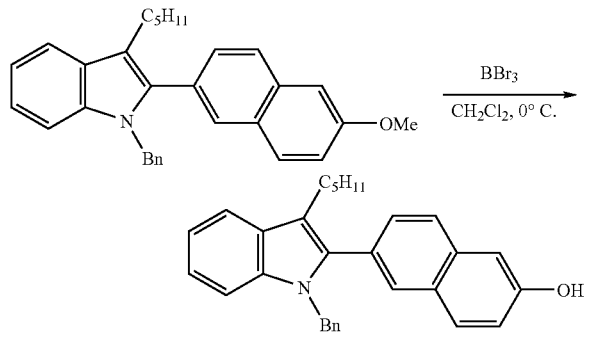

In such processes, a solution of 1-benzyl-2-(6-methoxy-naphthalen-2-yl)-3-pentyl-1H-indole in methylene chloride generally is treated with 0.75 equivalents of boron tribromide in methylene chloride at 0° C., the resulting mixture is slowly heated to 25° C., and the reaction is quenched with a 5% solution of sodium hydroxide in water. The organic and aqueous layers are separated, and the organic layer is replaced with toluene. Heptane is added to the solution and the product is crystallized at 0° C. to produce 85% to 90% of 6-(1-benzyl-3-pentyl-1H-indol-2-yl)-naphthalen-2-ol.

The reaction depicted in Scheme 3 can be performed using alternative solvents, including chlorinated hydrocarbons, such as, for example, 1,2-dichloroethane; and aromatic hydrocarbons, such as, for example, xylenes, alkylbenzenes, and alkyltoluenes. The reaction temperature in the process depicted in Scheme 3 can be much as 10° C. to 50° C. higher or lower than that indicated in the description provided above, depending upon the particular solvent used in the reaction.

The invention additionally relates to processes that include coupling substituted methyltetrazole with a substituted naphthol. Preferred processes are those in which the substituted methyltetrazole is directly coupled with the naphthol and the tetrazole is protected. In particularly preferred embodiments, the tetrazole is pyran-protected. In preferred embodiments, a compound of formula (2):

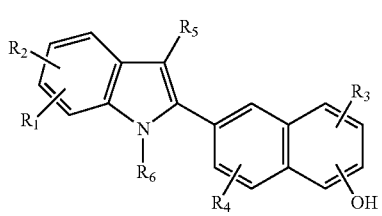

(2)

wherein $R_1$-$R_6$ are as defined herein;

is reacted with a compound of formula (3):

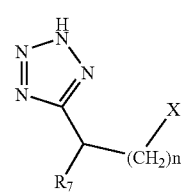

(3)

wherein

X is a leaving group and $R_7$ and n are as defined herein;

and an inorganic or organic base to produce a compound of formula (1):

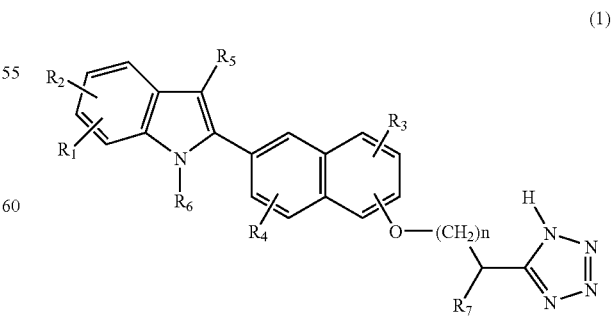

(1)

or a pharmaceutically acceptable salt thereof.

In preferred embodiments, the leaving group is a halogen or a sulfonate. In particularly preferred processes, the leaving group is chlorine and the compound of formula (3) is 5-chloromethyl-1H-tetrazole (CMT). In certain aspects of the invention, the 5-chloromethyl-1H-tetrazole (CMT) is protected with, for example, a dihydropyran. This can be effected, for example, by reacting 5-chloromethyl-1H-tetrazole (CMT) with 3,4-dihydro-3H-pyran (DHP) and pyridinium p-toluene sulfonate (PPTS) to produce tetrahydropyran (THP) protected 5-chloromethyl-1H-tetrazole (CMT).

In certain processes, the inorganic or organic base is an alkaline carbonate, an alkaline earth metal carbonate, an alkaline hydroxide, an alkaline earth metal hydroxide, an amine, a phosphine, or an anion exchange resin. In particularly preferred embodiments of the invention, the inorganic or organic base is an alkaline carbonate such as, for example, lithium carbonate, potassium carbonate, cesium carbonate, or sodium carbonate.

In certain embodiments, the compound of formula (1) is a compound of formula (1a):

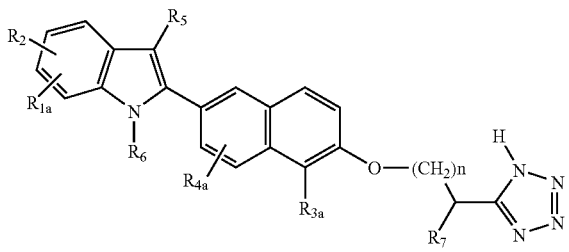

(1a)

Preferred compounds of formula (1a) are those of formula (1b):

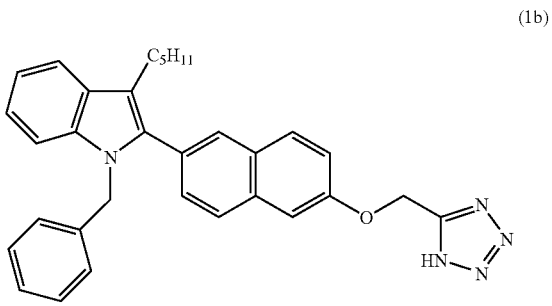

(1b)

Particularly preferred processes according to the invention involve coupling chloromethyltetrazole with a substituted naphthol, as depicted in Scheme 4, below.

Scheme 4

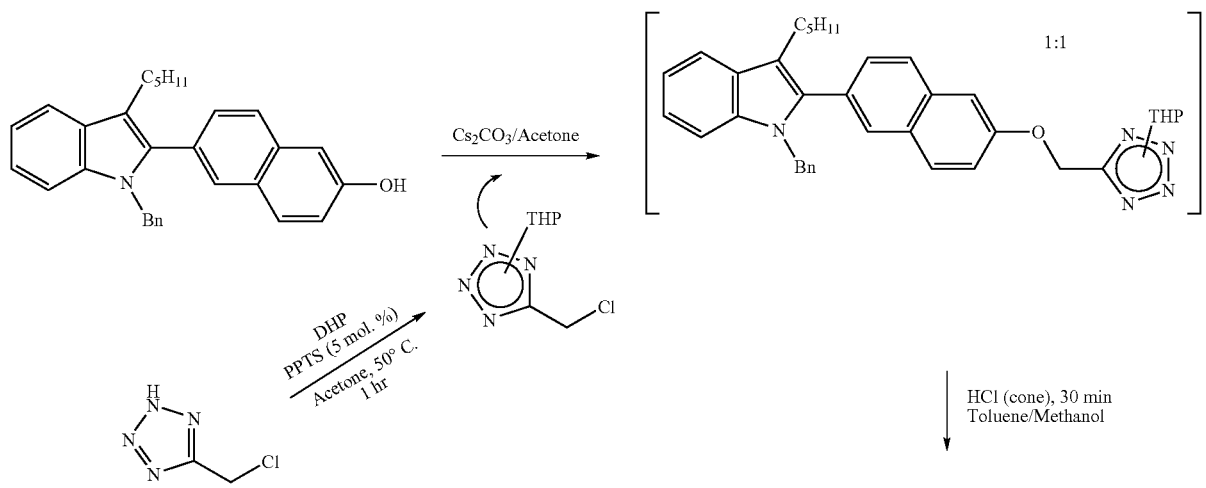

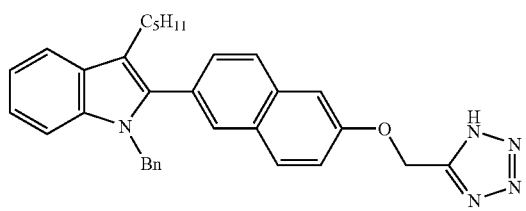

Crystalline 6-(1-benzyl-3-pentyl-1H-indol-2-yl)-naphthalen-2-ol preferably is added to a solution of tetrahydropyran (THP)-protected 5-chloromethyl-1H-tetrazole (CMT) in acetone. Cesium carbonate at 0° C. is then added to the mixture and the suspension is heated at a reflux temperature for four hours. Acetone is exchanged with toluene and the resulting suspension is quenched with hydrochloric acid and washed with water. The solution is treated with concentrated hydrochloric acid and methanol at 20° C. Toluene, followed by water, is added to the solution. The aqueous and organic layers are separated and the organic layer is washed with water. Crystallization at 20° C. yields 70% of 1-benzyl-3-pentyl-2-[6-(1H-tetrazol-5-ylmethoxy)-naphthalen-2-yl]-1H-indole.

In certain embodiments of the invention, the 1-benzyl-3-pentyl-2-[6-(1H-tetrazol-5-ylmethoxy) -naphthalen-2-yl]-1H-indole is recrystallized, preferably with ethyl acetate and heptane. In particularly preferred embodiments, the 1-benzyl-3-pentyl-2-[6-(1H-tetrazol-5-ylmethoxy)-naphthalen-2-yl]-1H-indole is recrystallized by dissolving the compound in ethyl acetate and adding heptane to initiate crystallization. Additional heptane is then added, the suspension is stirred, and is then filtered. The resultant cake is washed with a mixture of ethyl acetate and heptane and dried.

In one aspect, the invention provides multi-step processes for the preparation of substituted naphthylindole derivatives that can be used as plasminogen activator inhibitor-1 (PAI-1) inhibitors. Such processes comprise one or more of the forgoing steps of converting a compound of formula (6) to a compound of formula (5), converting a compound of formula (5) to a compound of formula (4), converting a compound of formula (4) to a compound of formula (2), and converting a compound of formula (2) to a compound of formula (1) or a pharmaceutically acceptable salt thereof.

One particularly preferred process for preparing substituted naphthylindole derivatives that can be used as inhibitors of plasminogen activator inhibitor-1(PAI-1), is depicted in Scheme 5, below.

Scheme 5

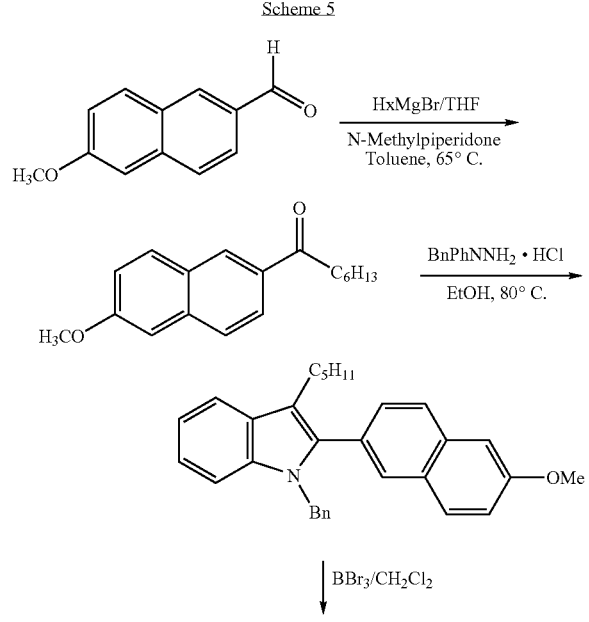

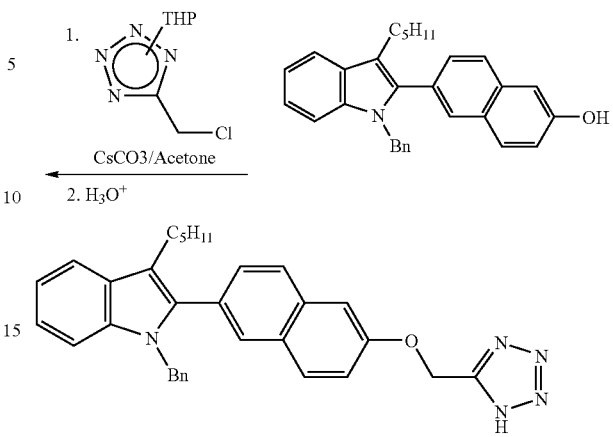

The following examples are illustrative of certain embodiments of the invention and should not be considered to limit the scope of the invention.

EXAMPLE 1

Preparation of 1-(6-methoxy-naphthalen-2-yl)heptan-1-one using hexylmagnesium bromide

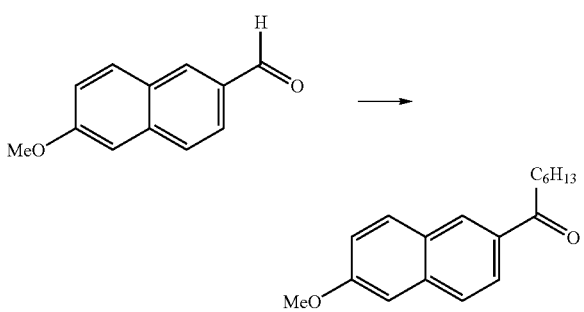

A 2.0 M solution of hexylmagnesium bromide in THF (31 mL, 62 mmol) was cooled to 0° C. A solution of 2-methoxy-6-naphthaldehyde (10.0 g, 53.7 mmoles) in toluene (71 mL) was added to the pre-cooled hexylmagnesium bromide solution under an inert atmosphere over 10 minutes, while maintaining the temperature of the solution in the range of −2° C. to +2° C. The solution was stirred for 20 min at 0° C., treated with 1-methyl-4-piperidone (MPP, 1.34 g, 11.8 mmoles, 0.22 mol-equiv.), and heated to 65° C. Additional MPP (103 g, 91.3 mmoles, 1.70 mol-equiv.) was added at 65° C. over 11 hours at the general rate of 0.15 mol-equiv./h (9.1 g/h). The resulting solution was cooled and 10% hydrochloric acid (88.1 g, 0.242 moles) was added at a rate sufficient to maintain the temperature below 30° C. The emulsion was stirred for an additional 10 minutes, the layers were separated, and the aqueous layer was removed (pH 1). The organic layer was dried with magnesium sulfate (4 g), filtered, and concentrated in vacuo to yield 14.2 g (98%) of a light-yellow solid as the title compound with 97.8% ar. HPLC purity.

EXAMPLE 2

Preparation of 1-(6-Methoxy-naphthalen-2-yl)heptan-1-one using hexyllithium

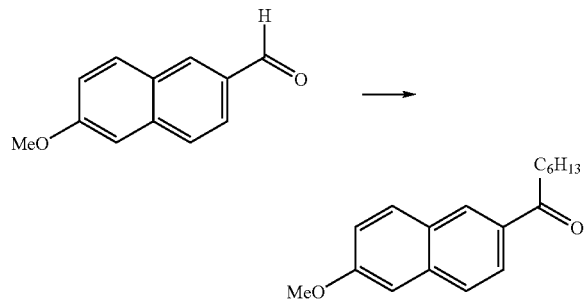

A 2.3 M solution of hexyllithium in hexane (0.29 L, 0.67 moles) was cooled to −15° C. A solution of 2-methoxy-6-naphthaldehyde (104 g, 0.559 moles) in toluene (0.60 L) was added to the pre-cooled hexyllithium solution under an inert atmosphere over 1.5 hours, while maintaining the temperature in the range of −10° C. to −15° C. Magnesium sulfate (78.0 g, 0.644 moles) was added to the resulting brown hazy solution, bringing the temperature up to −5° C. After 15 minutes, MPP (14.0 g, 0.124 moles, 0.22 mol-equiv.) was added to the solution over a period of less than two minutes, which changed the solution's color from brown to light yellow and raised the solution's temperature to 4° C. The suspension was heated to 65° C. and additional MPP (119 g, 1.05 moles, 1.88 mol-equiv.) was added over 6.5 hours at the general rate of 0.29 mol-equiv./h (18.3 g/h). The mixture was cooled and 10% hydrochloric acid (900 g, 2.47 moles) was added at a rate sufficient to maintain the temperature below 30° C. During the HCl addition the reaction mixture cleared, a viscous phase formed on the bottom of the solution, and both phases turned red. When about half the acid was added, the color of the solution changed to bright yellow (water layer pH 6). Once all the acid was added, the mixture became a homogeneous emulsion. The emulsion was stirred for an additional 30 minutes, the layers were separated, and the bottom layer was drained (pH 1). The upper layer was washed with water (0.3 kg), the bottom aqueous layer was separated (pH 3), and the residual solution was concentrated in vacuo to 0.3 L. Octane (1.07 L) was added to the resulting solution, while maintaining the temperature of the solution at 60° C., and the mixture was concentrated in vacuo to 0.75 L. The solution was cooled to −3° C. (crystallization starts at ca. 40° C.) and stirred for 30 minutes at that temperature. The resultant light yellow suspension was filtered, dried in a nitrogen stream on a filter for 30 minutes, and the solids were vacuumed at 50° C./50 mm Hg, which yielded 117 g (77.5%) of the title compound as a light-yellow crystalline material with 97.9% ar. HPLC purity.

EXAMPLE 3

Preparation of 1-Benzyl-2-(6-methoxynaphthalen-2-yl)-3-pentyl-1H-indole

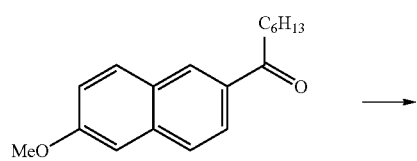

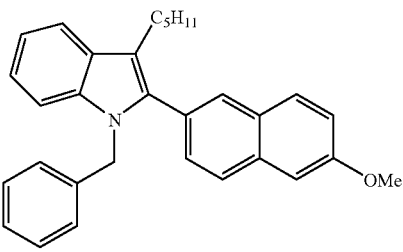

1-(6-methoxy-naphthalen-2-yl)heptan-1-one (0.176 kg, 0.651 moles) was dissolved in anhydrous ethanol (1.56 L), 1-benzyl-1-phenylhydrazine hydrochloride (BPH, 0.168 kg, 0.716 moles) was added, a 37% aqueous solution of hydrochloric acid (1.2 g, 12.2 mmoles) was added, and the reaction mixture was heated under reflux for 7 hours. Two portions of BPH (8.4 g, 71.6 mmoles each) were added to the mixture at one hour intervals at 70° C. The temperature of the mixture returned to the reflux temperature after the first BPH addition. Heating was terminated, the reaction mixture was diluted with heptane (1.65 L) followed by water (0.62 kg), and the mixture was stirred for 30 minutes while maintaining the temperature at 45° C. The addition of heptane resulted in the precipitation of solids from the homogeneous organic phase, while the addition of water brought the mixture to a biphasic state with layers in an approximate ratio of 1:1. The bottom layer was drained (pH 1) and the upper layer was washed with water (0.26 kg) while stirring the mixture for 30 minutes. The bottom layer was again drained (pH 3) and the upper layer was cooled to 12° C. in the reactor. All operations subsequent to the quenching step were conducted at 45° C. to prevent premature product crystallization. About 10 grams of the chilled solution were withdrawn from the reactor, subjected to low-temperature crystallization, and returned to the chilled solution as a seeding suspension. The mixture was kept at 12° C. for 30 minutes, cooled to −10° C. over two hours, and stirred at that temperature for 30 minutes. The suspension was filtered, the solids were dried in a nitrogen stream on a filter for 30 minutes, and the solids were vacuumed at 50° C./50 mm Hg to yield 221 g (78%) of the title compound as light-yellow prills with 99.45% ar. HPLC purity.

EXAMPLE 4

Preparation of 1-benzyl-2-(6-hydroxynaphthalen-2-yl)-3-pentyl-1H-indole

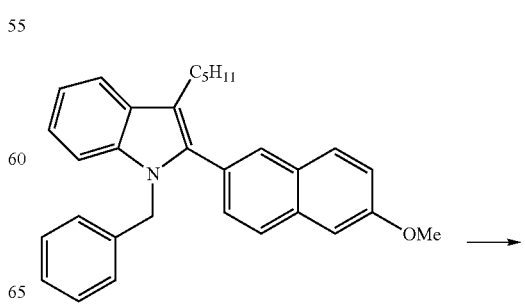

-continued

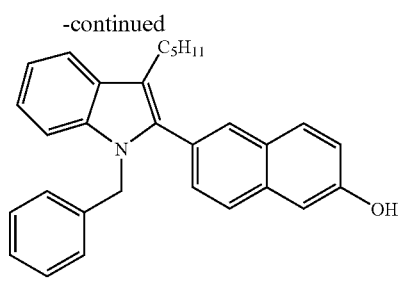

1-benzyl-2-(6-methoxynaphthalen-2-yl)-3-pentyl-1H-indole (210.0 g, 0.484 mol) was dissolved in methylene chloride (620 mL), the solution was cooled to 0° C., and 1.0 M boron tribromide in methylene chloride (363 mL, 0.363 mole) was added to the solution over 30 minutes. The reaction mixture was stirred for twelve hours at 20° C. to 25° C., at which point in time HPLC analysis indicated that no starting material was present. The solution was cooled to 0° C.-10° C. and a 5% aqueous sodium hydroxide solution (462 mL, 0.605 mole) was added to the solution over 30 minutes. The mixture was stirred for 30 minutes and the layers were separated. The organic layer was washed with 15% aqueous sodium chloride (170 mL) and passed through a silica gel pad (210 g). The pad was washed with two 250 mL portions of methylene chloride. The combined filtrate was concentrated by atmospheric distillation to a volume of 500 mL, toluene (260 mL) was added, and distillation was resumed until the volume reached 500 mL. The temperature increased to 75° C.-80° C. during the distillation. Heptane (1040 mL) was then added while maintaining the temperature. The mixture was cooled to 55° C. over 50 min. Approximately 10 grams of the solution were withdrawn from the reactor, subjected to low-temperature crystallization, and returned to the solution as a seeding suspension at 55° C. Crystallization began at 43° C.-45° C. The suspension was cooled to 0° C.-5° C. and stirred at that temperature for two hours. The solid was filtered, washed with 500 mL heptane, and dried at 50° C./50 torr for 24 hours to produce 166.0 g (81.7% yield) of the title compound as an off-white solid with 99.89% ar. HPLC purity.

EXAMPLE 5

Preparation of 1-Benzyl-3-pentyl-2-[6-(1H-tetrazol-5-ylmethoxy)naphthalen-2-yl]-1H-indole

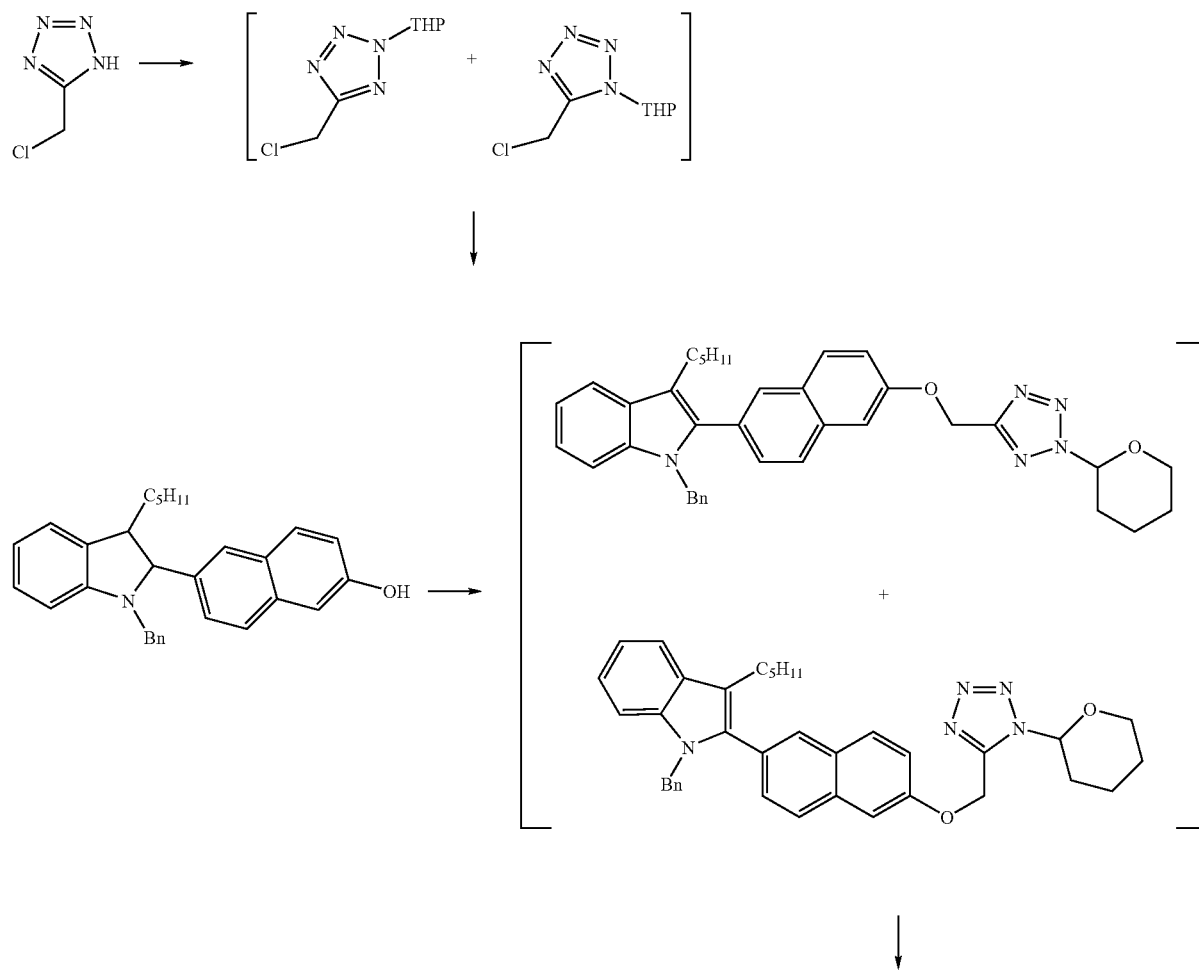

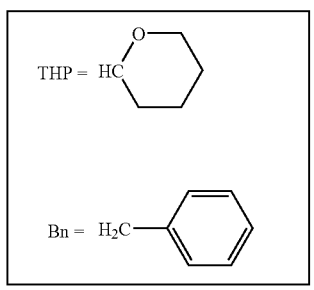

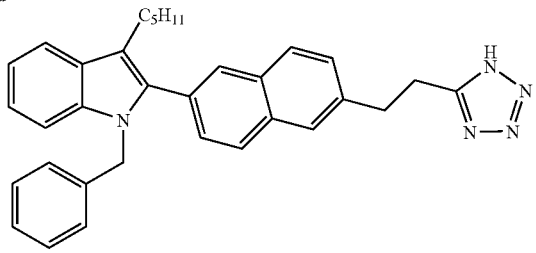

Pyridinium p-toluenesulfonate (0.16 kg, 0.64 mol) was added to a solution of 5-chloromethyl-1H-tetrazole (2.37 kg, 20.0 mol) and 3,4-dihydro-3H-pyran (2.83 kg, 33.6 mol) in acetone (20 L) and the resultant solution was heated at 45° C. for 3 hours. Additional 3,4-dihydro-3H-pyran (1.46 kg, 17.4 mol) was added and heating was continued for 2 hours. 1-benzyl-2-(6-hydroxynaphthalen-2-yl)-3-pentyl-1H-indole (7.0 kg, 16.7 mol) was added and the solution was stirred at 17° C. Cesium carbonate (6.77 kg, 20.8 mol) was then added. The temperature of the suspension was adjusted to 60° C. and heating was continued for 3 hours, at which time HPLC analysis showed 100% conversion. Toluene (55 L) was added and acetone was removed by atmospheric distillation. The mixture was heated to 100° C. to provide 35 L of residual volume. After cooling the residue to 20° C., a solution of 1 N hydrochloric acid (28.6 L) was added, the mixture was stirred for 30 minutes, and the layers were separated. The upper organic layer was treated with a mixture of concentrated hydrochloric acid (8.3 kg, 84.2 mol) and methanol (28 L) at 20° C. for 30 minutes, the time necessary to complete hydrolysis, followed by dilution with toluene (58 L). A 1 N sodium hydroxide solution (35 L) was added, which changed the pH to 4. The layers were separated and the upper organic layer was washed with a 17% sodium chloride solution (35 L) at 40° C. The toluene layer was slowly cooled to −3° C. (crystallization begins at 21° C.) while being stirred for 1 hour. The suspension was then filtered, and the cake was washed with cold toluene (−3° C., 40 L) to yield, after drying, 6.4 kg (76.4% yield) of the title compound as an off-white solid with 99.26% ar. HPLC purity.

EXAMPLE 6

Re-crystallization of 1-Benzyl-3-pentyl-2-[6-(1H-tetrazol-5-ylmethoxy)naphtha-len-2-yl]-1H-indole Crude 1-benzyl-3-pentyl-2-[6-(1H-tetrazol-5-ylmethoxy)naphtha-len-2-yl]-1H-indole (6.4 kg) was dissolved in ethyl acetate (22 L) at 38° C., the solution was cooled to 22° C., and the solution was passed through a 10-µm filter cartridge. Heptane (20 L) was added to the resultant solution at 23° C. to initiate crystallization. As soon crystallization began, more heptane (28 L) was added, the suspension was stirred for 19 hours, and the suspension was then filtered on a Nutsche filter. The cake was washed with a mixture of ethyl acetate (6.4 L) and heptane (13.2 L) and dried in the filter using a nitrogen stream for 18 hours, to provide 4.4 kg (68.8%) of the title API with 99.76% ar. HPLC purity, 0.019% of residual heptane and no detectable ethyl acetate or toluene.

The entire disclosure of each patent, patent application, and publication cited or described in this document is hereby incorporated herein by reference.

What is claimed is:

1. A process comprising reacting a compound of formula (2):

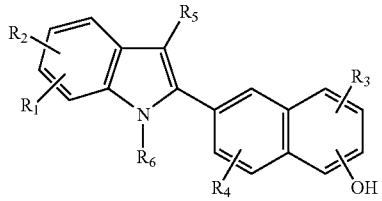

wherein:
$R_1$, $R_2$, $R_3$, and $R_4$ are each, independently, hydrogen, alkyl of 1 to 3 carbon atoms, cycloalkyl of 3 to 5 carbon atoms, —CH$_2$cycloalkyl of 4 to 6 carbon atoms, alkanoyl of 2 to 4 carbon atoms, halogen, hydroxyl, aryl of 6 to 14 carbon atoms optionally substituted with 1 to 3 $R_8$ groups, perfluoroalkyl of 1 to 3 carbon atoms, alkoxy of 1 to 3 carbon atoms, amino, alkylamino of 1 to 3 carbon atoms, dialkylamino of 1 to 3 carbon atoms, or perfluoroalkoxy of 1 to 3 carbon atoms;
$R_5$ is hydrogen, alkyl of 1 to 6 carbon atoms, perfluoroalkyl of 1 to 6 carbon atoms, aryl of 6 to 14 carbon atoms optionally substituted with 1 to 3 $R_8$ groups, alkanoyl of 2 to 7 carbon atoms, or aroyl of 7 to 15 carbon atoms optionally substituted with 1 to 3 $R_8$ groups;
$R_6$ is hydrogen, alkyl of 1 to 6 carbon atoms, alkylaryl of 8 to 20 carbon atoms, benzyl optionally substituted with 1 to 3 $R_8$ groups, alkanoyl of 2 to 7 carbon atoms, or aroyl of 7 to 15 carbon atoms optionally substituted with 1 to 3 $R_8$ groups; and
$R_8$ is hydrogen, alkyl of 1 to 3 carbon atoms, cycloalkyl of 3 to 5 carbon atoms, —CH$_2$cycloalkyl of 4 to 6 carbon atoms, alkanoyl of 2 to 4 carbon atoms, halogen, hydroxy, perfluoroalkyl of 1 to 3 carbon atoms, alkoxy of 1 to 3 carbon atoms, amino, alkylamino of 1 to 3 carbon atoms, dialkylamino of 1 to 3 carbon atoms, or perfluoroalkoxy of 1 to 3 carbon atoms;
with a compound of formula (3):

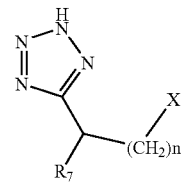

wherein
X is a leaving group;
$R_7$ is hydrogen, alkyl of 1 to 6 carbon atoms, alkylaryl of 7 to 20 carbon atoms, or aryl of 6 to 14 carbon atoms optionally substituted with 1 to 3 $R_8$ groups; and
n is an integer from 0 to 6;

and an inorganic or organic base, to produce a compound of formula (1):

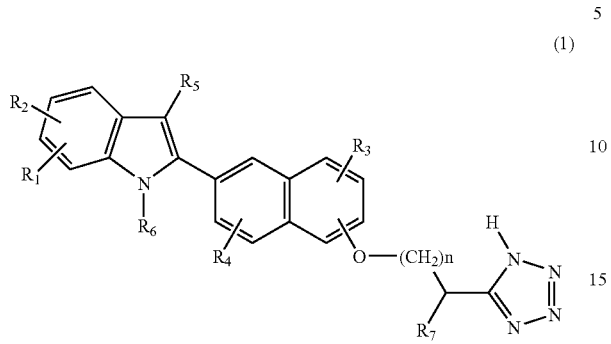

(1)

or a pharmaceutically acceptable salt thereof.

2. The process of claim 1 wherein X is a halogen or a sulfonate.

3. The process of claim 1 wherein the compound of formula (3) is 5-chloromethyl-1 H-tetrazole (CMT).

4. The process of claim 3 further comprising reacting the 5-chloromethyl-1H-tetrazole (CMT) with 3,4-dihydro-3H-pyran (DHP) and pyridinium p-toluene sulfonate (PPTS) to produce tetrahydropyran (THP) protected 5-chloromethyl-1H-tetrazole (CMT) prior to reaction with the compound of formula (2).

5. The process of claim 1 wherein the inorganic or organic base is an alkaline carbonate, an alkaline earth metal carbonate, an alkaline hydroxide, an alkaline earth metal hydroxide, an amine, a phosphine, or an anion exchange resin.

6. The process of claim 5 wherein the alkaline carbonate is lithium carbonate, potassium carbonate, cesium carbonate, or sodium carbonate.

7. The process of claim 1 wherein the compound of formula (2) is a compound of formula (2a):

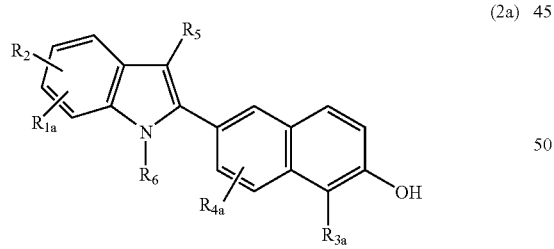

(2a)

wherein $R_{1a}$, $R_{3a}$, and $R_{4a}$ are each, independently, hydrogen, alkyl of 1 to 3 carbon atoms, cycloalkyl of 3 to 5 carbon atoms, alkanoyl of 2 to 4 carbon atoms, halogen, hydroxyl, aryl of 6 to 14 carbon atoms optionally substituted with 1 to 3 $R_8$ groups, perfluoroalkyl of 1 to 3 carbon atoms, alkoxy of 1 to 3 carbon atoms, amino, alkylamino of 1 to 3 carbon atoms, dialkylamino of 1 to 3 carbon atoms, or perfluoroalkoxy of 1 to 3 carbon atoms.

8. The process of claim 7 wherein the compound of formula (2a) is a compound of formula (2b):

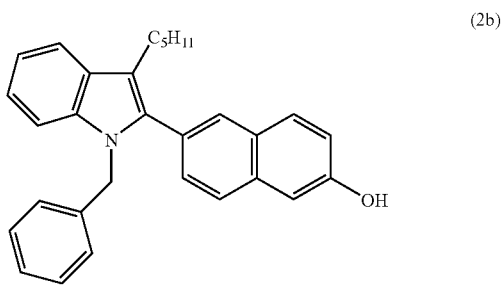

(2b)

9. The process of claim 1 further comprising reacting a compound of formula (4):

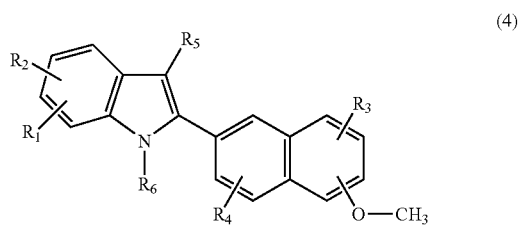

(4)

with an ether demethylating agent to produce a compound of formula (2).

10. The process of claim 9 wherein the ether demethylating agent is boron tribromide ($BBr_3$).

11. The process of claim 9 further comprising reacting a compound of formula (5):

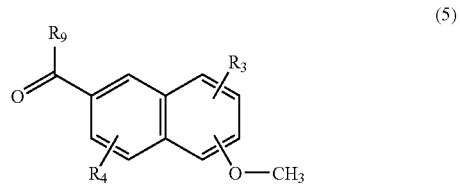

(5)

wherein
$R_9$ is —$CH_2$—$R_5$;
with a substituted hydrazine of the formula:

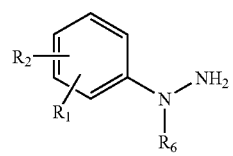

to produce a compound of formula (4).

12. The process of claim 11 wherein the substituted hydrazine is 1-benzyl-1-phenylhydrazine hydrochloride (BPH).

13. The process of claim 11 further comprising reacting a compound of formula (6):

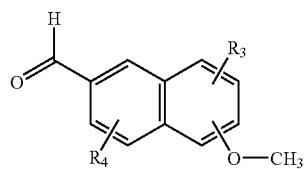

(6)

with an alkylmagnesium halide or an arylmagnesium halide of the formula $R_9MgBr$ and further with a hydride acceptor to produce a compound of formula (5).

14. The process of claim 13 wherein the alkylmagnesium halide is hexylmagnesium bromide (HxMgBr).

15. The process of claim 11 further comprising reacting a compound of formula (6):

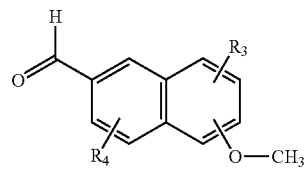

(6)

consecutively with an alkyllithium of the formula $R_9Li$, a magnesium salt, and a hydride acceptor to produce a compound of formula (5).

16. The process of claim 15 wherein the alkyllithium is hexyllithium.

17. The process of claims 15 wherein the magnesium salt is magnesium bromide, magnesium chloride, a magnesium sulfonate, or magnesium sulfate.

18. The process of claim 13 wherein the hydride acceptor is an optionally substituted dialkylaminobenzaldehyde or an optionally substituted aminocycloalkanone.

19. The process of claim 18 wherein the hydride acceptor is 1-methyl-4-piperidone (MPP).

* * * * *